United States Patent [19]

Buchecker et al.

[11] Patent Number: 5,662,829
[45] Date of Patent: Sep. 2, 1997

[54] FLUOROCYCLOHEXENE-DIOXANE DERIVATIVES

[75] Inventors: Richard Buchecker, Zurich, Switzerland; Guy Marck, Rixheim, France

[73] Assignee: Rolic AG, Basel, Switzerland

[21] Appl. No.: 606,117

[22] Filed: Feb. 23, 1996

[30] Foreign Application Priority Data

Mar. 3, 1995 [CH] Switzerland ................. 608/95

[51] Int. Cl.⁶ ................. C09K 19/34; C07D 319/06
[52] U.S. Cl. ................. 252/299.61; 549/369
[58] Field of Search ................. 252/299.61; 549/369

[56] References Cited

U.S. PATENT DOCUMENTS

| | | | |
|---|---|---|---|
| 4,212,815 | 7/1980 | Boswell, Jr. | 260/397.2 |
| 4,565,425 | 1/1986 | Petrzilka et al. | 359/56 X |
| 4,676,604 | 6/1987 | Petrzilka | 349/186 X |
| 4,983,479 | 1/1991 | Broer et al. | 430/20 |
| 5,013,578 | 5/1991 | Petrzilka | 252/299.63 |
| 5,254,698 | 10/1993 | Coates et al. | 549/369 |
| 5,322,638 | 6/1994 | Schadt et al. | 252/299.61 |
| 5,356,560 | 10/1994 | Rerffenrath et al. | 252/299.61 |
| 5,447,658 | 9/1995 | Buchecker et al. | 252/299.6 |
| 5,560,863 | 10/1996 | Reiffenrath et al. | 252/299.01 |

FOREIGN PATENT DOCUMENTS

| | | |
|---|---|---|
| 122389 | 2/1984 | European Pat. Off. |
| 433836 | 12/1990 | European Pat. Off. |
| 42 26 772 | 8/1992 | Germany |

OTHER PUBLICATIONS

Derwent Abstract No. 88-320124/45. (Mar. 1987).
Japanese Chemical Abstract No. 111:48298r; (1989).
*Organic Reactions*, 35, 531 (1988).
Japanese Chemical Astract No. 110:125657; (1988).

*Primary Examiner*—C. H. Kelly
*Attorney, Agent, or Firm*—George W. Johnston; William H. Epstein; John P. Parise

[57] ABSTRACT

Compounds of the following formula are useful as liquid crystals:

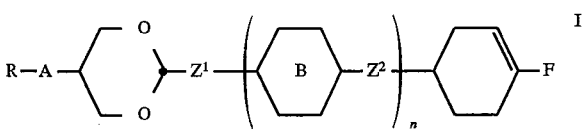

wherein
  R is a $C_1$-$C_{12}$ alkyl or a $C_2$-$C_{12}$ alkenyl;
  A is a single bond or trans-1,4-cyclohexylene;
  $Z^1$ and $Z^2$ are independently a single bond or —$CH_2CH_2$—, except $Z^1$ and $Z^2$ cannot simultaneously be —$CH_2CH_2$—;
  ring B is trans-1,4-cyclohexylene or 1,4-phenylene; and
  n is 0 or 1, Liquid crystalline mixtures which contain such compounds are especially useful in electro-optical indicating devices.

29 Claims, No Drawings

FLUOROCYCLOHEXENE-DIOXANE DERIVATIVES

BACKGROUND OF THE INVENTION

1. Field

The present invention is concerned with novel liquid crystalline fluorocyclohexene-dioxane derivatives, liquid crystalline mixtures which contain such compounds, and the use of such compounds and mixtures in electro-optical devices.

2. Description

The optical properties of liquid crystals can be influenced by applied voltage, contributing to the use of liquid crystals primarily as dielectrics in display devices. Liquid crystals electro-optical devices are well-known to persons skilled in the art and can utilize various effects. Examples of such devices include cells having dynamic scattering, DAP cells ("deformed aligned phase"), guest/host cells, TN cells ("twisted nematic"), STN cells ("super twisted nematic"), SBE cells ("super birerefringence effect"), and OMI cells ("optical mode interference"). In displays having a high information content, actively controlled cells, such as TFT cells ("thin film transistor"), have joined passively controlled-multiplexed cells, and have recently become important to the industry. However, most common indicating devices are still based on the Schadt-Helfrich effect and have a twisted nematic structure.

To be useful, liquid crystal materials should have good chemical, photochemical and thermal stability, as well as good stability in electric fields. Further, they should have a suitable mesophase over the broadest range possible (for example, a nematic or a cholesteric phase for the cells referred to above). Nevertheless, liquid crystal materials should have a sufficiently low viscosity and should permit the production of mixtures having short response times, low threshold potentials, and high contrast. Further properties, such as the electrical conductivity, dielectric anisotropy, and optical anisotropy, must fulfill different requirements depending on the field of application and type of cell. For example, materials for twisted nematic cells should have a positive dielectric anisotropy which is as high as possible while simultaneously having a conductivity which is as low as possible. This latter property is of particular importance for TFT cells. Unfortunately, components having a high dielectric anisotropy typically yield mixtures having increased conductivity because of their improved capacity to dissolve ionic impurities. Accordingly, components having a dielectric anisotropy and a low conductivity are highly sought.

Compounds having a surprisingly high dielectric anisotropy and simultaneously a low conductivity as well as a relatively small optical anisotropy are provided by the present invention.

SUMMARY OF THE INVENTION

The subject invention provides a compound of the formula:

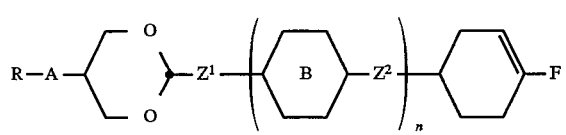

wherein

R is a $C_1$–$C_{12}$ alkyl or a $C_2$–$C_{12}$ alkenyl;

A is a single bond or trans-1,4-cyclohexylene;

$Z^1$ and $Z^2$ are independently a single bond or —$CH_2CH_2$—, except that $Z^1$ and $Z^2$ cannot simultaneously be —$CH_2CH_2$—;

ring B is trans-1,4-cyclohexylene or 1,4-phenylene; and n is 0 or 1.

DETAILED DESCRIPTION OF THE INVENTION

The subject invention will now be described in terms of its preferred embodiments. These embodiments are set forth to aid in understanding the invention, but are not to be construed as limiting.

These are compounds of the formula

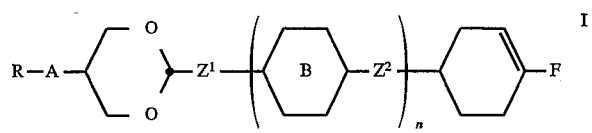

wherein

R signifies alkyl or alkenyl with a maximum of 12 carbon atoms;

A signifies a single bond or trans-1,4-cyclohexylene;

$Z^1$ and $Z^2$ signify a single bond or —$CH_2CH_2$—;

ring B signifies trans-1,4-cyclohexylene or 1,4-phenylene; and n is 0 or 1; with the proviso that $Z^1$ and $Z^2$ can not simultaneously be —$CH_2CH_2$—.

The term "alkyl or alkenyl with a maximum of 12 carbon atoms" signifies in the scope of the present invention straight-chain or branched (optionally chiral) alkyl groups or 1E-alkenyl, 3E-alkenyl or alkenyl groups having a terminal double bond. These groups have a maximum of 12, preferably, however, a maximum of 7, carbon atoms. These are, for example, methyl, ethyl, propyl, butyl, pentyl, hexyl, heptyl, isopropyl, 2-methyl-butyl, 2-methyl-pentyl, 2-methyl-hexyl, vinyl, 1E-propenyl, 1E-butenyl, 1E-pentenyl, 1E-hexenyl, 1E-heptenyl, 3-butenyl, 3E-pentenyl, 3E-hexenyl, heptenyl, 4-pentenyl, 5-hexenyl, 6-heptenyl and the like.

Preferred compounds in accordance with the invention are of the formulas

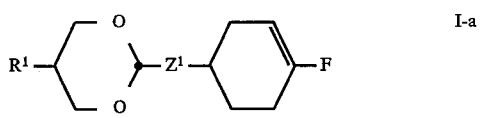

I-a

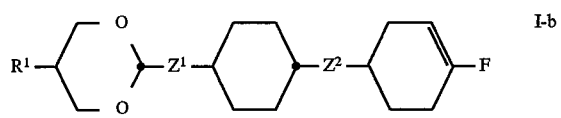

I-b

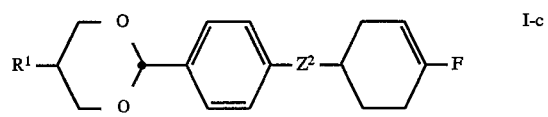

I-c

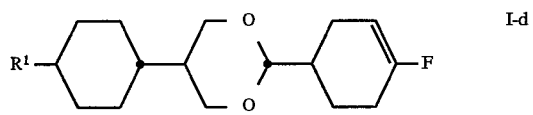

I-d wherein $R^1$ signifies straight-chain alkyl or straight-chain 1E- or 3E-alkenyl with a maximum of 7 carbon atoms; and $Z^1$ and $Z^2$ are as defined above.

Compounds of formulae I-a, I-b and I-c are especially preferred, particularly where $Z^1$ and $Z^2$, if present, signify a single bond, that is, compounds of the formulas

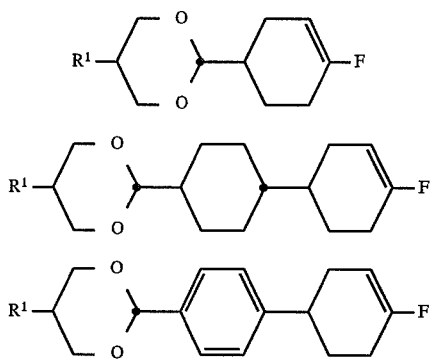

wherein $R^1$ has the aforementioned significance.

Compounds of formulas I and I-a, I-b and I-c as well as compounds of formulas I-a1, I-b1 and I-c1 in which $R^1$ signifies ethyl, propyl, butyl, pentyl, vinyl, 1E-propenyl, 1E-butenyl, 1E-pentenyl, 3-butenyl, 3E-pentenyl or 4-pentenyl are particularly preferred.

The compounds of formula I can be produced in a manner known per se, for example in the manner set forth in Scheme 1 in which the symbols given in the formulae correspond to the aforementioned significances. Thus, for example, the fluorination of the ketones 1 with diethylaminosulphur trifluoride (DAST) to the fluorocyclohexenes 2 can be carried out analogously to the procedure which is described in U.S. Pat. No. 4,212,815, the contents of which are hereby incorporated by reference, or in Organic Reactions 35, 531 (1988). The reaction is preferably carried out in polar, aprotic, inert solvents such as dimethoxyethane, diglyme, dioxan and the like at temperatures from about 20° C. to about 50° C. The formation of geminal difluorocyclohexane derivatives can be suppressed, for example, by the addition of a catalytic amount of acid such as oleum or trifluoromethanesulphonic acid. The further reaction steps, i.e. the reduction of the ester 2 to the aldehyde 3 and the subsequent acetalization with a diol 4, which lead to the dioxanes of formula I, are standard methods of organic chemistry and will be known to any person skilled in the art.

Scheme 1

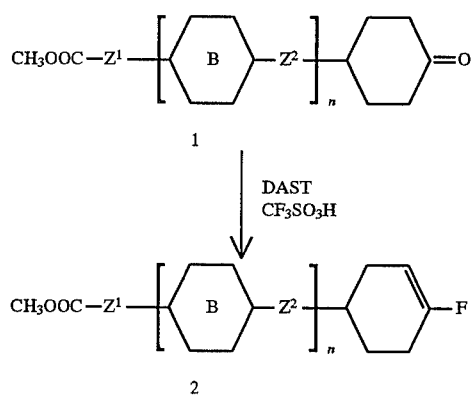

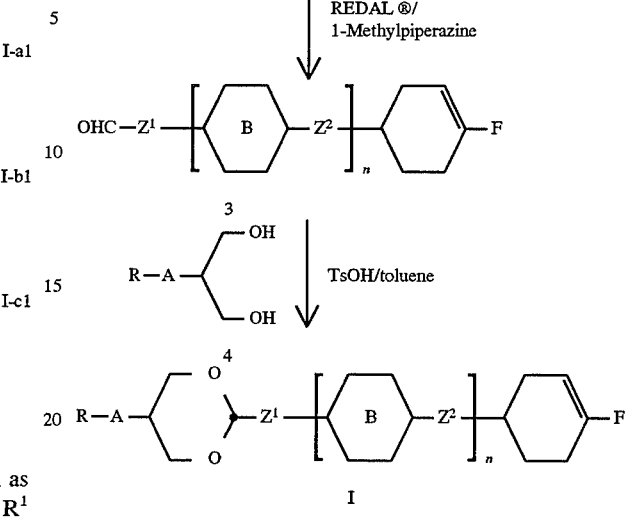

The ketones 1 as well as the diols 4 are known or are analogues of known compounds and can be prepared according to known methods. Thus, the preparation of the ketones 1 is described in detail in the literature, for example in EP-A 122 389, corresponding to U.S. Pat. Nos. 4,565,425, 4,676,604, and 5,013,478, the contents of each of which are herein incorporated by reference. Further, diols 4 are generally used in the production of 1,3-dioxanes in liquid crystal chemistry and many of them have been described, for example in EP-A 433 836 which corresponds to U.S. Pat. No. 5,322,638, the contents of which is herein incorporated by reference.

The compounds of formula I can be used in the form of mixtures with one another and/or with other liquid crystal components.

The invention is therefore also concerned with liquid crystalline mixtures having at least 2 components, with at least one component being a compound of formula I. Suitable liquid crystal components will be known to a person skilled in the art in large numbers, for example from D. Demus et at., Flüssige Kristalle in Tabellen, VEB Deutscher Verlag für Grundstoffindustrie, Leipzig, Volumes I und II. Moreover, many of these compounds are commercially available.

The compounds in accordance with the invention are distinguished by their chemical stability in mixtures. Having regard to the good solubility of the compounds of formula I in accordance with the invention in other liquid crystal materials and having regard to their good miscibility with one another, the content of compounds of formula I in the mixtures in accordance with the invention can be relatively high and can be, for example, about 1–70 wt. %. In general, a content of about 3–40 wt. %, especially of about 5–20 wt. %, of compounds of formula I is preferred.

Preferably, the mixtures in accordance with the invention contain, in addition to one or more compounds of formula I, one or more compounds from the group of compounds of the formulas

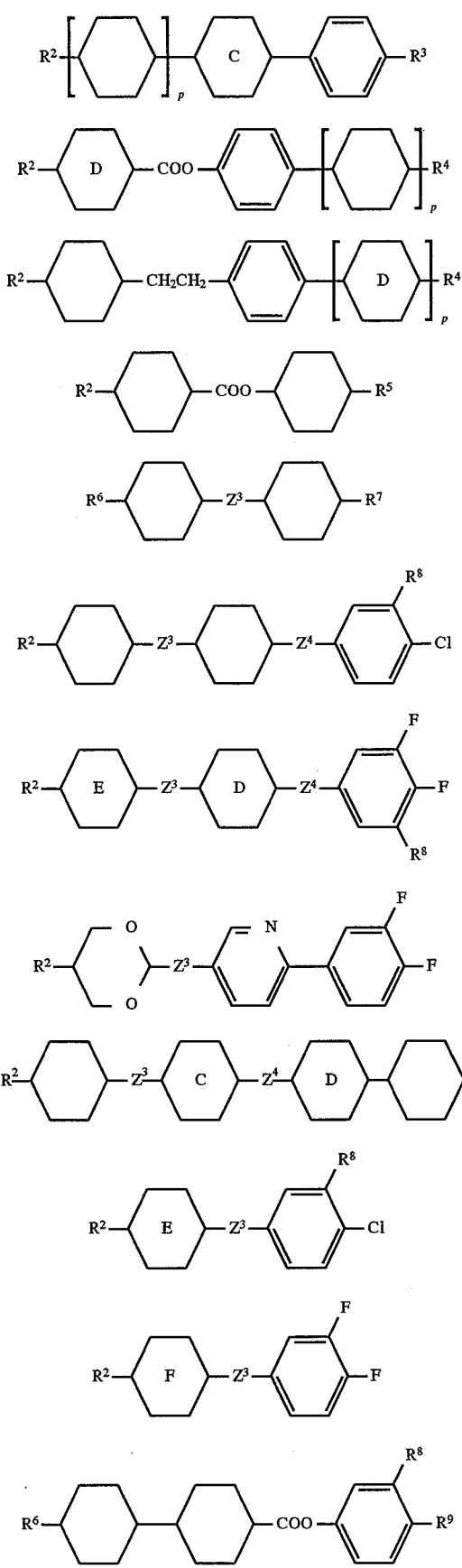

wherein
- $R^2$ and $R^5$ signify alkyl, alkoxyalkyl, 3E-alkenyl, 4-alkenyl or on saturated rings also 1E-alkenyl;
- p signifies 0 or 1;
- ring C signifies 1,4-phenylene, trans-1,4-cyclohexylene or trans-1,3-dioxane-2,5-diyl;
- $R^3$ signifies fluorine, alkyl, 3E-alkenyl, 4-alkenyl, alkoxy, 2E-alkenyloxy, 3-alkenyloxy or 1-alkynyl;
- ring D signifies 1,4-phenylene or trans-1,4-cyclohexylene;
- $R^4$ signifies alkyl, 3E-alkenyl, 4-alkenyl or on trans-1,4-cyclohexylene also 1E-alkenyl or on 1,4-phenylene also alkoxy, 2E-alkenyloxy or 3-alkenyloxy;
- $R^6$ signifies alkyl, 1E-alkenyl, 3E-alkenyl or 4-alkenyl;
- $R^7$ signifies cyano, alkyl, 1E,-alkenyl, 3E,-alkenyl, 4-alkenyl, alkoxy, 2E-alkenyloxy, 3-alkenyloxy, alkoxymethyl or (2E-alkenyl)oxymethyl;
- $Z^3$ and $Z^4$ signify a single covalent bond or $-CH_2CH_2-$, with two aromatic rings always being linked by a single covalent bond;
- ring E signifies trans-1,4-cyclohexylene or trans-1,3-dioxane-2,5-diyl;
- $R^8$ signifies hydrogen or fluorine;
- $R^9$ signifies fluorine or chlorine; and
- ring F signifies trans-1,4-cyclohexylene or trans-1,3-dioxane-2,5-diyl.

The terms used in connection with the compounds of formulas II to XV are explained hereinafter.

"Aromatic rings" denotes rings such as, for example, 1,4-phenylene, pyridine-2,5-diyl or pyrimidine-2,5-diyl.

"Saturated rings" denotes trans-1,4-cyclohexylene or trans-1,3-dioxane-2,5-diyl.

"Alkyl" signifies preferably straight-chain groups with 1 to 12 carbon atoms, especially preferred residues having 1 to 7 carbon atoms such as, for example, methyl, ethyl, propyl, butyl, pentyl, hexyl or heptyl.

"Alkyloxyalkyl" signifies preferably straight-chain residues such as, for example, methoxymethyl, ethoxymethyl, propyloxymethyl, butyloxymethyl and the like.

"Alkoxy" signifies preferably straight-chain residues such as, for example, methoxy, ethoxy, propyloxy, butyloxy, pentyloxy, hexyloxy, heptyloxy and the like.

"1E-Alkenyl" signifies preferably straight-chain alkenyl residues in which the double bond is situated in the 1-position such as, for example, vinyl, 1E-propenyl, 1E-butenyl, 1E-pentenyl, 1E-hexenyl, 1E-heptenyl and the like.

"3E-Alkenyl" signifies preferably straight-chain alkenyl residues in which the double bond is situated in the 3-position such as, for example, 3-butenyl, 3E-pentenyl, 3E-hexenyl, 3E-heptenyl and the like.

"4-Alkenyl" signifies preferably straight-chain alkenyl residues in which the double bond is situated in the 4-position such as, for example, 4-pentenyl, 4-hexenyl, 4-heptenyl and the like.

"2E- or 3-Alkenyloxy" signifies in this connection preferably straight-chain alkenyloxy residues in which the double bond is situated in the 2- or 3-position and E or Z indicates the preferred configuration such as, for example, allyloxy, 2E-butenyloxy, 2E-pentenyloxy, 2E-hexenyloxy, 2E-heptenyloxy, 3-butenyloxy, 3-pentenyloxy, 3-hexenyloxy, 3-heptenyloxy, 4-pentenyloxy, 5-hexenyloxy, 6-heptenyloxy and the like.

"1-Alkynyl" signifies in this connection preferably straight-chain alkynyl residues in which the triple bond is situated in the 1-position such as, for example, ethynyl, 1-propynyl, 1-butynyl, 1-pentynyl and the like.

The mixtures in accordance with the invention can also contain optically active compounds (e.g. optically active 4'-alkyl- or 4'-alkoxy-4-biphenylcarbonitriles) and/or dichroic dyes (e.g. azo, azoxy or anthraquinone dyes). The content of such compounds is determined by the solubility, the desired helical pitch, color, extinction and the like. In general, the content of optically active compounds and dichroic dyes is a maximum of in each case about 10 wt. % in the total mixture.

The production of the liquid crystalline mixtures and of the electro-optical devices can be effected in a manner known per se.

The production of the compounds of formula I as well as liquid crystalline mixtures containing these compounds is illustrated in more detail by the following Examples. C signifies a crystalline phase, S signifies a smectic phase, N signifies a nematic phase and I signifies the isotropic phase. $V_{10}$ denotes the voltage for 10% transmission (viewing direction perpendicular to the plate surface). $t_{on}$ and $t_{off}$ denote, respectively, the switching-on time and the switching-off time and Dn denotes the optical anisotropy.

Unless identified to the contrary, the experiments in the Examples below have actually been conducted.

EXAMPLE 1 a) 8.9 ml of sodium bis(2-methoxyethoxy)-aluminum hydride and 9 ml of toluene were cooled to 0° C. while gassing with nitrogen and treated within 30 minutes with a solution of 4.15 ml of 1-methylpiperazine in 20 ml of toluene. This solution was stirred at 0° C. for a further 30 minutes and subsequently added dropwise within 45 minutes to a solution, cooled to −50° C., of 3.0 g of methyl trans-4-(4-fluoro-cyclohex-3-enyl) cyclohexanecarboxylate in 40 ml of toluene. After stirring at −50° C. for 2 hours the reaction mixture was treated with 20 ml of ethanol and poured into a 10% sodium tartrate solution. The organic phase was extracted twice with water. The aqueous phase was extracted twice with ether and the organic phases were combined, dried over magnesium sulphate, filtered and the filtrate was evaporated. The residue was purified on silica gel (5% ethyl acetate/cyclohexane) and gave 1.77 g of trans-4-(4-fluoro-cyclohexane) cyclohexanecarbaldehyde.

b) 500 mg of trans-4-(4-fluoro-cyclohex-3-enyl) cyclohexanecarbaldehyde, 310 mg of 2-propyl-propane-1,3-diol and 50 mg of p-toluenesulphonic acid in 8 ml of toluene were boiled at reflux for 1 hour in an apparatus which was gassed with nitrogen and which was fitted with a water separator. After cooling the reaction solution was partitioned in water/ether. The organic phase was washed twice with water. The aqueous phases were extracted twice with ether. The organic phases were combined, dried over magnesium sulphate, filtered and the filtrate was evaporated. The crude product was recrystallized several times from ethanol/1% ethyl acetate and gave 350 mg of trans-2-[trans-4-(4-fluoro-cyclohex-3-enyl) cyclohexyl]-5-propyl-[1,3]-dioxane, m.p. (C-N)<room temperature; S-N 104° C., cl.p. (N-I) 118.3° C.;

The following compounds can be produced in an analogous manner.

trans-2-[trans-4-(4-Fluoro-cyclohex-3-enyl)cyclohexyl]-5-ethyl-[1,3]-dioxane, trans-2-[trans-4-(4-fluoro-cyclohex-3-enyl)cyclohexyl]-5-butyl-[1,3]-dioxane, trans-2-[trans-4-(4-fluoro-cyclohex-3-enyl)cyclohexyl]-5-pentyl-[1,3]-dioxane, trans-2-[trans-4-(4-fluoro-cyclohex-3-enyl)cyclohexyl]-5-vinyl-[1,3]-dioxane, trans-2-[trans-4-(4-fluoro-cyclohex-3-enyl)cyclohexyl]-5-(prop-1E-enyl)-[1,3]-dioxane, trans-2-[trans-4-(4-fluoro-cyclohex-3-enyl)cyclohexyl]-5-(but-3-enyl)-[1,3]-dioxane, trans-2-[trans-4-(4-fluoro-cyclohex-3-enyl)cyclohexyl]-5-(pent-1E-enyl)-[1,3]-dioxane, trans-2-[trans-4-(4-fluoro-cyclohex-3-enyl)cyclohexyl]-5-(but-3-enyl)-[1,3]-dioxane, trans-2-[trans-4-(4-fluoro-cyclohex-3-enyl)cyclohexyl]-5-(pent-3E-enyl)-[1,3]-dioxane, trans-2-[4-(4-fluoro-cyclohex-3-enyl)phenyl]-5-ethyl-[1,3]-dioxane, trans-2-[4-(4-fluoro-cyclohex-3-enyl)phenyl]-5-propyl-[1,3]-dioxane, trans-2-[4-(4-fluoro-cyclohex-3-enyl)phenyl]-5-butyl-[1,3]-dioxane, trans-2-[4-(4-fluoro-cyclohex-3-enyl)phenyl]-5-pentyl-[1,3]-dioxane, trans-2-[4-(4-fluoro-cyclohex-3-enyl)phenyl]-5-vinyl-[1,3]-dioxane, trans-2-[4-(4-fluoro-cyclohex-3-enyl)phenyl]-5-(prop-1E-enyl)-[1,3]-dioxane, trans-2-[4-(4-fluoro-cyclohex-3-enyl)phenyl]-5-(but-1E-enyl)-[1,3]-dioxane, trans-2-[4-(4-fluoro-cyclohex-3-enyl)phenyl]-5-(pent-1E-enyl)-[1,3]-dioxane, trans-2-[4-(4-fluoro-cyclohex-3-enyl)phenyl]-5-(but-3-enyl)-[1,3]-dioxane, trans-2-[4-(4-fluoro-cyclohex-3-enyl)phenyl]-5-(pent-3E-enyl)-[1,3]-dioxane, trans-2-(4-fluoro-cyclohex-3-enyl)-5-ethyl-[1,3]-dioxane, trans-2-(4-fluoro-cyclohex-3-enyl)-5-propyl-[1,3]-dioxane, trans-2-(4-fluoro-cyclohex-3-enyl)-5-butyl-[1,3]-dioxane, trans-2-(4-fluoro-cyclohex-3-enyl)-5-pentyl-[1,3]-dioxane, trans-2-(4-fluoro-cyclohex-3-enyl)-5-vinyl-[1,3]-dioxane, trans-2-(4-fluoro-cyclohex-3-enyl)-5-( prop-1E-enyl )-[1,3]-dioxane, trans-2-(4-fluoro-cyclohex-3-enyl)-5-(but-1E-enyl)-[1,3]-dioxane, trans-2-(4-fluoro-cyclohex-3-enyl)-5-(pent-1E-enyl)-[1,3]-dioxane, trans-2-(4-fluoro-cyclohex-3-enyl)-5-(but-3-enyl)-[1,3]-dioxane, trans-2-(4-fluoro-cyclohex-3-enyl)-5-(pent-3E-enyl)-[1,3]-dioxane, trans-2-(4-fluoro-cyclohex-3-enyl )-5-(trans-4-ethyl-cyclohexyl)-[1,3]-dioxane, trans-2-(4-fluoro-cyclohex-3-enyl)-5-(trans-4-propyl-cyclohexyl)-[1,3]-dioxane, trans-2-(4-fluoro-cyclohex-3-enyl)-5-(trans-4-butyl-cyclohexyl)-[1,3]-dioxane, trans-2-(4-fluoro-cyclohex-3-enyl)-5-(trans-4-pentyl-cyclohexyl)-[1,3]-dioxane, trans-2-(4-fluoro-cyclohex-3-enyl)-5-(trans-4-vinyl-cyclohexyl)-[1,3]-dioxane, trans-2-(4-fluoro-cyclohex-3-enyl)-5-[trans-4-(prop-1E-enyl)-cyclohexyl]-[1,3]-dioxane, trans-2-(4-fluoro-cyclohex-3-enyl)-5-[trans-4-(but-1E-enyl)-cyclohexyl]-[1,3]-dioxane, trans-2-(4-fluoro-cyclohex-3-enyl)-5-[trans-4-(pent-1E-enyl)-cyclohexyl]-[1,3]-dioxane, trans-2-(4-fluoro-cyclohex-3-enyl)-5-[trans-4-(but-3-enyl)-cyclohexyl]-[1,3]-dioxane, trans-2-(4-fluoro-cyclohex-3-enyl)-5-[trans-4-(pent-3E-enyl)-cyclohexyl]-[1,3]-dioxane, trans-2-[2-(4-fluoro-cyclohex-3-enyl)ethyl]-5-ethyl-[1,3]-dioxane, trans-2-[2-(4-fluoro-cyclohex-3-enyl)ethyl]-5-propyl-[1,3]-dioxane, trans-2-[2-(4-fluoro-cyclohex-3-enyl)ethyl]-5-butyl-[1,3]-dioxane, trans-2-[2-(4-fluoro-cyclohex-3-enyl)ethyl]-5-pentyl-[1,3]-dioxane, trans-2-[2-(4-fluoro-cyclohex-3-enyl)ethyl]-5-vinyl-[1,3]-dioxane, trans-2-[2-(4-fluoro-cyclohex-3-enyl)ethyl]-5-(prop-1E-enyl)-[1,3]-dioxane, trans-2-[2-(4-fluoro-cyclohex-3-enyl)ethyl]-5-(but-1E-enyl)-[1,3]-dioxane, trans-2-[2-(4-fluoro-cyclohex-3-enyl)ethyl]-5-(pent-1E-enyl)-[1,3]-dioxane, trans-2-[2-(4-fluoro-cyclohex-3-enyl)ethyl]-5-(but-3-enyl)-[1,3]-dioxane, trans-2-[2-(4-fluoro-cyclohex-3-enyl)ethyl]-5-(pent-3E-enyl)-[1,3]-dioxane, trans-2-{2-[trans-4-(4-fluoro-cyclohex-3-enyl)cyclohexyl]ethyl}-5-ethyl-[1,3]-dioxane, trans-2-{2-[trans-4-(4-fluoro-cyclohex-3-enyl)cyclohexyl]ethyl}-5-propyl-[1,3]-dioxane, trans-2-{2-[trans-4-(4-fluoro-cyclohex-3-enyl)cyclohexyl]ethyl}-5-butyl-[1,3]-dioxane, trans-2-{2-[trans-4-(4-fluoro-cyclohex-3-enyl)cyclohexyl]ethyl}-5-pentyl-[1,3]-dioxane, trans-2-{2-[trans-4-(4-fluoro-cyclohex-3-enyl)cyclohexyl]ethyl}-5-vinyl-[1,3]-dioxane, trans-2-{2-[trans-4-(4-fluoro-cyclohex-3-enyl)cyclohexyl]ethyl}-5-(prop -1E-enyl)-[1,3]-dioxane, trans-2-{2-[trans-4-(4-fluoro-cyclohex-3-enyl)cyclohexyl]ethyl}-5-(but-1E-enyl)-[1,3]-dioxane, trans-2-{2-[trans-4-(4-fluoro -cyclohex-3-enyl)cyclohexyl]ethyl}-5-(pent-1E-enyl)-[1,3]-dioxane, trans-2-{2-[trans-4-(4-fluoro-cyclohex-3-enyl)cyclohexyl]ethyl}-5-(but-3-enyl)-[1,3]-dioxane, trans-2-{2-[trans-4-(4-fluoro-cyclohex-3-enyl)cyclohexyl]ethyl}-5-(pent-3E-enyl)-[1,3]-dioxane, trans-2-{4-[2-(4-fluoro-cyclohex-3-enyl)ethyl]phenyl}-5-ethyl-[1,3]-dioxane, trans-2-{4-[2-(4-fluoro-cyclohex-3-enyl)ethyl]phenyl}-5-propyl-[1,3]-dioxane, trans-2-{4-[2-(4-fluoro-cyclohex-3-enyl)ethyl]phenyl}-5-butyl-[1,3]-dioxane, trans-2-{4-[2-(4-fluoro-cyclohex-3-enyl)ethyl]phenyl}-5-pentyl-[1,3]-dioxane, trans-2-{4-[2-(4-fluoro-cyclohex-3-enyl)ethyl]phenyl}-5-vinyl-[1,3]-dioxane, trans-2-{4-[2-(4-fluoro-cyclohex-3-enyl)ethyl]phenyl}-(prop-1E-enyl)-[1,3]-dioxane, trans-2-{4-[2-(4-fluoro-cyclohex-3-enyl)ethyl]phenyl}-5-(but-E-enyl)-[1,3]-dioxane, trans-2-{4-[2-(4-fluoro-cyclohex-3-enyl)ethyl]phenyl}-5-(pent-1E-enyl)-[1,3]-dioxane, trans-2-{4-[2-(4-fluoro-cyclohex-3-enyl)ethyl]phenyl}-5-(but-3-enyl)-[1,3]-dioxane, trans-2-{4-[2-(4-fluoro-cyclohex-3-enyl)ethyl]phenyl}-5-(pent-3E-enyl)-[1,3]-dioxane, trans-2-{4-[2-(4-fluoro-cyclohex-3-enyl)ethyl]cyclohexyl}-5-ethyl-[1,3]-dioxane, trans-2-{4-[2-(4-fluoro-cyclohex-3-enyl)ethyl]cyclohexyl}-5-propyl-[1,3]-dioxane, trans-2-{4-[2-(4-fluoro-cyclohex-3-enyl)ethyl]cyclohexyl}-5-pentyl-[1,3]-dioxane, trans-2-{4-[2-(4-fluoro-cyclohex-3-enyl)ethyl]cyclohexyl}-5-(prop-1E-enyl)-[1,3]-dioxane.

EXAMPLE 2

Binary mixtures (BM) with 4-(trans-4-pentylcyclohexyl)benzonitrile were prepared in order to investigate the properties of the compounds of formula I in mixtures. The threshold potential and the response times were measured at 22° C. in a TN cell (low bias tilt) having a plate separation of 8 μm; the 2.5-fold value of the threshold potential ($V_{10}$) was chosen as the operating voltage. The corresponding data for 4-(trans-4-pentyl-cyclohexyl)benzonitrile are: cl.p. (N-I)=54.6° C., $V_{10}$=1.62 V, $t_{on}$=22 ms, $t_{off}$=42 ms, Δn=0.120.

BM-1

90 wt. % of 4-(trans-4-pentyl-cyclohexyl)benzonitrile 10 wt. % of trans-2-[trans-4-(4-fluoro-cyclohex-3-enyl)cyclohexyl]-5-propyl-[1,3]-dioxane cl.p. (N/I): 55.9° C., $V_{10}$=1.54 V, $t_{on}$=29 ms, $t_{off}$=47 ms, Δn=0.114

BM-2

80 wt. % of 4-(trans-4-pentyl-cyclohexyl)benzonitrile 20 wt. % of trans-2-[trans-4-(4-fluoro-cyclohex-3-enyl)cyclohexyl]-5-propyl-[1,3]-dioxane cl.p. (N/I): 58.2° C., $V_{10}$=1.49 V, $t_{on}$=34 ms, $t_{off}$=55 ms, Δn=0.107

The subject invention has been described in terms of its preferred embodiments. Upon reading the present specification, various alternative embodiments will become obvious to the skilled artisan. These compounds are to be considered within the scope and spirit of the subject invention which is only to be limited by the claims which follow and their equivalents.

What is claimed is:

1. A compound of the formula:

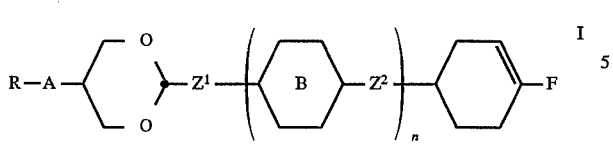

wherein

R is a $C_1$–$C_{12}$ alkyl or a $C_2$–$C_{12}$ alkenyl;

A is a single bond or trans-1,4-cyclohexylene;

$Z^1$ and $Z^2$ are independently a single bond or —$CH_2CH_2$—, except that $Z^1$ and $Z^2$ cannot simultaneously be —$CH_2CH_2$—;

ring B is trans-1,4-cyclohexylene or 1,4-phenylene; and n is 0 or 1.

2. The compound according to claim 1 of the formula:

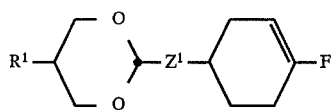

wherein $R^1$ is a straight-chain $C_1$–$C_7$ alkyl or a straight-chain $C_2$–$C_7$ 1E- or $C_4$–$C_7$ 3E-alkenyl.

3. The compound according to claim 1 of the formula:

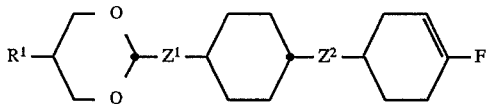

wherein $R^1$ is a straight-chain $C_1$–$C_7$ alkyl or a straight-chain $C_2$–$C_7$ 1E- or $C_4$–$C_7$ 3E-alkenyl.

4. The compound according to claim 1 of the formula:

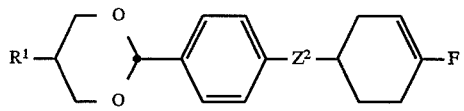

wherein $R^1$ is a straight-chain $C_1$–$C_7$ alkyl or a straight-chain $C_2$–$C_7$ 1E- or $C_4$–$C_7$ 3E-alkenyl.

5. The compound according to claim 1 of the formula:

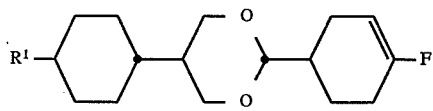

wherein $R^1$ is a straight-chain $C_1$–$C_7$ alkyl or a straight-chain $C_2$–$C_7$ 1E- or $C_4$–$C_7$ 3E-alkenyl.

6. The compound according to claim 1, wherein both $Z^1$ and $Z^2$ are single bonds.

7. The compound according to claim 2, wherein both $Z^1$ and $Z^2$ are single bonds.

8. The compound according to claim 3, wherein both $Z^1$ and $Z^2$ are single bonds.

9. The compound according to claim 4, wherein both $Z^1$ and $Z^2$ are single bonds.

10. The compound according to claim 5, wherein both $Z^1$ and $Z^2$ are single bonds.

11. The compound according to claim 2 of the formula:

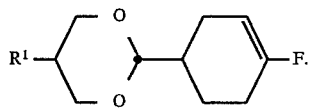

12. The compound according to claim 3 of the formula:

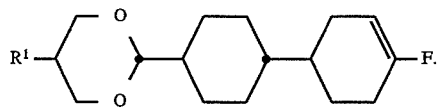

13. The compound according to claim 4 of the formula:

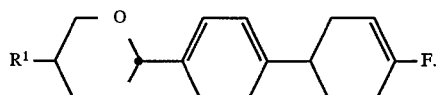

14. The compound according to claim 1, wherein $R^1$ is selected from the group consisting of ethyl, propyl, butyl, pentyl, vinyl, 1E-propenyl, 1E-butenyl, 1E-pentenyl, 3-butenyl, 3E-pentenyl, and 4-pentenyl.

15. The compound according to claim 2, wherein $R^1$ is selected from the group consisting of ethyl, propyl, butyl, pentyl, vinyl, 1E-propenyl, 1E-butenyl, 1E-pentenyl, 3-butenyl, 3E-pentenyl, and 4-pentenyl.

16. The compound according to claim 3, wherein $R^1$ is selected from the group consisting of ethyl, propyl, butyl, pentyl, vinyl, 1E-propenyl, 1E-butenyl, 1E-pentenyl, 3-butenyl, 3E-pentenyl, and 4-pentenyl.

17. The compound according to claim 4, wherein $R^1$ is selected from the group consisting of ethyl, propyl, butyl, pentyl, vinyl, 1E-propenyl, 1E-butenyl, 1E-pentenyl, 3-butenyl, 3E-pentenyl, and 4-pentenyl.

18. The compound according to claim 5, wherein $R^1$ is selected from the group consisting of ethyl, propyl, butyl, pentyl, vinyl, 1E-propenyl, 1E-butenyl, 1E-pentenyl, 3-butenyl, 3E-pentenyl, and 4-pentenyl.

19. The compound according to claim 6, wherein $R^1$ is selected from the group consisting of ethyl, propyl, butyl, pentyl, vinyl, 1E-propenyl, 1E-butenyl, 1E-pentenyl, 3-butenyl, 3E-pentenyl, and 4-pentenyl.

20. The compound according to claim 7, wherein $R^1$ is selected from the group consisting of ethyl, propyl, butyl, pentyl, vinyl, 1E-propenyl, 1E-butenyl, 1E-pentenyl, 3-butenyl, 3E-pentenyl, and 4-pentenyl.

21. The compound according to claim 8, wherein $R^1$ is selected from the group consisting of ethyl, propyl, butyl, pentyl, vinyl, 1E-propenyl, 1E-butenyl, 1E-pentenyl, 3-butenyl, 3E-pentenyl, and 4-pentenyl.

22. The compound according to claim 9, wherein $R^1$ is selected from the group consisting of ethyl, propyl, butyl, pentyl, vinyl, 1E-propenyl, 1E-butenyl, 1E-pentenyl, 3-butenyl, 3E-pentenyl, and 4-pentenyl.

23. The compound according to claim 10, wherein $R^1$ is selected from the group consisting of ethyl, propyl, butyl, pentyl, vinyl, 1E-propenyl, 1E-butenyl, 1E-pentenyl, 3-butenyl, 3E-pentenyl, and 4-pentenyl.

24. The compound according to claim 11, wherein $R^1$ is selected from the group consisting of ethyl, propyl, butyl, pentyl, vinyl, 1E-propenyl, 1E-butenyl, 1E-pentenyl, 3-butenyl, 3E-pentenyl, and 4-pentenyl.

25. The compound according to claim 12, wherein $R^1$ is selected from the group consisting of ethyl, propyl, butyl, pentyl, vinyl, 1E-propenyl, 1E-butenyl, 1E-pentenyl, 3-butenyl, 3E-pentenyl, and 4-pentenyl.

26. The compound according to claim 13, wherein $R^1$ is selected from the group consisting of ethyl, propyl, butyl, pentyl, vinyl, 1E-propenyl, 1E-butenyl, 1E-pentenyl, 3-butenyl, 3E-pentenyl, and 4-pentenyl.

27. A liquid crystalline mixture having at least 2 components, wherein at least one component is a compound of formula:

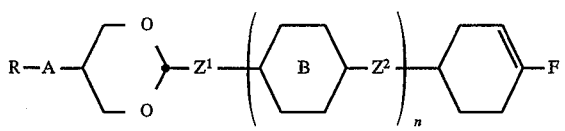

wherein

R is a $C_1$–$C_{12}$ alkyl or a $C_2$–$C_{12}$ alkenyl;

A is a single bond or trans-1,4-cyclohexylene;

$Z^1$ and $Z^2$ are independently a single bond or —$CH_2CH_2$—; except that $Z^1$ and $Z^2$ cannot simultaneously be —$CH_2CH_2$—;

ring B is trans-1,4-cyclohexylene or 1,4-phenylene; and n is 0 or 1.

28. The liquid crystalline mixture according to claim 27, wherein the content of compound of formula I is from about 1 to about 70 wt. %.

29. The liquid crystalline mixture according to claim 28, wherein the content of compound of formula I is from about 5 to about 20 wt. %.

* * * * *